(12) United States Patent
Tameishi et al.

(10) Patent No.: US 6,497,692 B1
(45) Date of Patent: *Dec. 24, 2002

(54) INDIVIDUALLY PACKAGED ABSORBENT ARTICLE

(75) Inventors: Kazuaki Tameishi, Hyogo (JP); Nami Terada, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/787,447

(22) PCT Filed: Oct. 5, 1998

(86) PCT No.: PCT/US98/21024

§ 371 (c)(1),
(2), (4) Date: Mar. 19, 2001

(87) PCT Pub. No.: WO00/19954

PCT Pub. Date: Apr. 13, 2000

(51) Int. Cl.[7] ................................................ A61F 13/15
(52) U.S. Cl. ........................ 604/385.02; 604/385.01; 604/385.02; 604/387; 604/397
(58) Field of Search ........................... 604/385, 385.02, 604/385.01, 385.04, 387, 397

(56) References Cited

U.S. PATENT DOCUMENTS

| | | |
|---|---|---|
| 5,413,568 A | 5/1995 | Roach et al. |
| 5,569,230 A * | 10/1996 | Fisher et al. ............... 206/438 |
| 6,063,065 A * | 5/2000 | Costa ......................... 206/438 |
| 6,074,376 A | 6/2000 | Mills |

FOREIGN PATENT DOCUMENTS

| | | | |
|---|---|---|---|
| DE | 196 06 902 A1 | 8/1997 | |
| GB | 2 306 428 A | 5/1997 | |
| WO | WO 98/42285 A1 | 10/1998 | |
| WO | WO 00/19953 | * 4/2000 | ........... A61F/13/15 |
| WO | WO 00/19954 | * 4/2000 | ........... A61F/13/15 |

* cited by examiner

Primary Examiner—John J. Calvert
Assistant Examiner—Angela Grayson
(74) Attorney, Agent, or Firm—Matthew P. Fitzpatrick; Ingrid N. Hickman

(57) ABSTRACT

An individually packaged absorbent article is disclosed. The individually packaged absorbent article comprises an absorbent article and a wrapper. The absorbent article extends in a longitudinal direction and includes a main body portion having a pair of longitudinal side edges, a pair of end edges, a garment surface, and a body surface. The garment surface of the main body portion has a main fastener. The wrapper for the absorbent article has a main wrapper sheet and a main fastener cover. The body surface of the main body portion is disposed to face the main wrapper sheet. The main fastener of the main body portion is covered by the main fastener cover. The main fastener cover is joined to the main wrapper sheet. The main body portion and the wrapper are folded as a unit at least about one transverse axis such that the garment surface is oriented inwardly with respect to the folded unit. At least a part of the main fastener is exposed when the wrapper is opened.

10 Claims, 13 Drawing Sheets

INDIVIDUALLY PACKAGED ABSORBENT ARTICLE

FIELD

This invention relates to an individually packaged absorbent article.

BACKGROUND

Absorbent articles which are used to absorb body exudates, such as disposable diapers, adult incontinence products or sanitary napkins are well known. Such absorbent articles typically have a body surface which may include a liquid permeable topsheet, a garment surface which may include a liquid impermeable backsheet, and an absorbent therebetween. When the absorbent article is used, the body surface of the absorbent article is placed facing the wearer's body and the garment surface is placed against the wearer's undergarment. The body surface of the absorbent article must be kept hygienic prior to use of the absorbent article because the body surface directly touches the wearer's body. Typically, an absorbent article such as a sanitary napkin is individually wrapped by a wrapper to protect the absorbent article from contamination. Such individually packaged absorbent articles are disclosed in, for example, JP Utility Model Laid-open publication 95/39820 published on Jul. 18, 1995, JP Utility Model Laid-open publication 94/75446 published on Oct. 25, 1994, and JP Patent Laid-open publication 91/176376 published on Jul. 31, 1991. In certain known designs, an absorbent article such as a sanitary napkin is folded into three portions such that the body surface of the sanitary napkin is oriented inwardly to the folded sanitary napkin and the garment surface is wrapped by a wrapper. The garment surface of the sanitary napkin also includes a main fastener, which is covered by the wrapper, to secure the sanitary napkin to the undergarment. In these absorbent articles, the body surface is protected from contact by the wearer's hands before the sanitary napkin is unfolded for application to the wearer's undergarment. However, the wearer must open and remove the wrapper from the sanitary napkin and unfold the sanitary napkin when applying the sanitary napkin to the wearer's undergarment. In the configuration where the wrapper and the sanitary napkin are opened, the main fastener of the sanitary napkin is still covered by the wrapper and is not exposed while the body surface of the sanitary napkin is exposed. Therefore, the wearer must remove the wrapper from the sanitary napkin to expose the main fastener. During this process, the wearer may touch the body surface of the sanitary napkin. This causes body surface contamination. In addition, while the wearer applies the sanitary napkin to the undergarment after removing the wrapper, the wearer tends to apply the sanitary napkin by touching the body surface and/or by pushing the body surface of the sanitary napkin toward the undergarment to secure the main fastener provided on the garment surface to the undergarment. This also causes body surface contamination. Thus, there is no convenient means to protect the body surface of the sanitary napkin while the wearer removes the wrapper from the sanitary napkin and applies the sanitary napkin to the undergarment.

Attempts to protect the body surface of the sanitary napkin during the application of the sanitary napkin to the undergarment have been made. For example, JP Patent Laid-open publication 96/56989 discloses an absorbent article such as a sanitary napkin having a surface cover sheet covering the body surface of the main body portion of the sanitary napkin. This sanitary napkin also has a release paper covering adhesive provided on the garment surface of the sanitary napkin. The wearer must remove the release paper covering the adhesive of the garment surface before the wearer applies the sanitary napkin to the undergarment. It is quite inconvenient for the wearer.

Base on the foregoing, there is a need for an absorbent article individually packaged by a wrapper having a main wrapper sheet wherein the body surface of the absorbent article remains protected from, e.g., the wearer's hands during unwrapping and application. None of the existing art provides all of the advantages and benefits of the present invention.

SUMMARY

The present invention provides an individually packaged absorbent article. The individually packaged absorbent article comprises an absorbent article and a wrapper. The absorbent article extends in a longitudinal direction and includes a main body portion having a pair of longitudinal side edges, a pair of end edges, a garment surface, and a body surface. The garment surface of the main body portion has a main fastener. The wrapper for the absorbent article has a main wrapper sheet and a main fastener cover. The body surface of the main body portion is disposed to face the main wrapper sheet. The main fastener of the main body portion is covered by the main fastener cover. The main fastener cover is joined to the main wrapper sheet. The main body portion and the wrapper are folded as a unit at least about one transverse axis such that the garment surface is oriented inwardly with respect to the folded unit. At least a part of the main fastener is exposed when the wrapper is opened.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION OF THE INVENTION

All cited references are incorporated herein by reference in their entireties. Citation of any reference is not an admission regarding any determination as to its availability as prior art to the claimed invention.

"Comprising" means that other steps and other elements which do not affect the end result can be added. This term encompasses the terms "consisting of" and "consisting essentially of".

Individually wrapped absorbent articles such as sanitary napkins are useful to protect the absorbent article from contamination. Such absorbent articles may be wrapped by a wrapper including a main wrapper sheet and a main fastener cover. The main wrapper sheet may be provided in order to protect a body surface of an absorbent article from contamination during application of the absorbent article to the undergarment. The main fastener cover may be provided in order to protect a main fastener provided on the garment surface of the absorbent articles. If the absorbent articles have two separate elements of material to protect portions of the absorbent articles and if the wearer must remove those elements separately prior to application process of the absorbent article to the undergarment, it is quite inconvenient for the wearer. The present invention answers the need for an individually wrapped absorbent article whose body surface remains protected from, e.g., the wearer's hands during application of the absorbent article. Additionally, the present invention provides an absorbent article having a main wrapper sheet and a main fastener cover in which the wearer does not have to give an extra step of removing the main fastener cover prior to application process of the absorbent article to the undergarment. These and other features of the present invention are discussed in more detail below.

Figure 1:
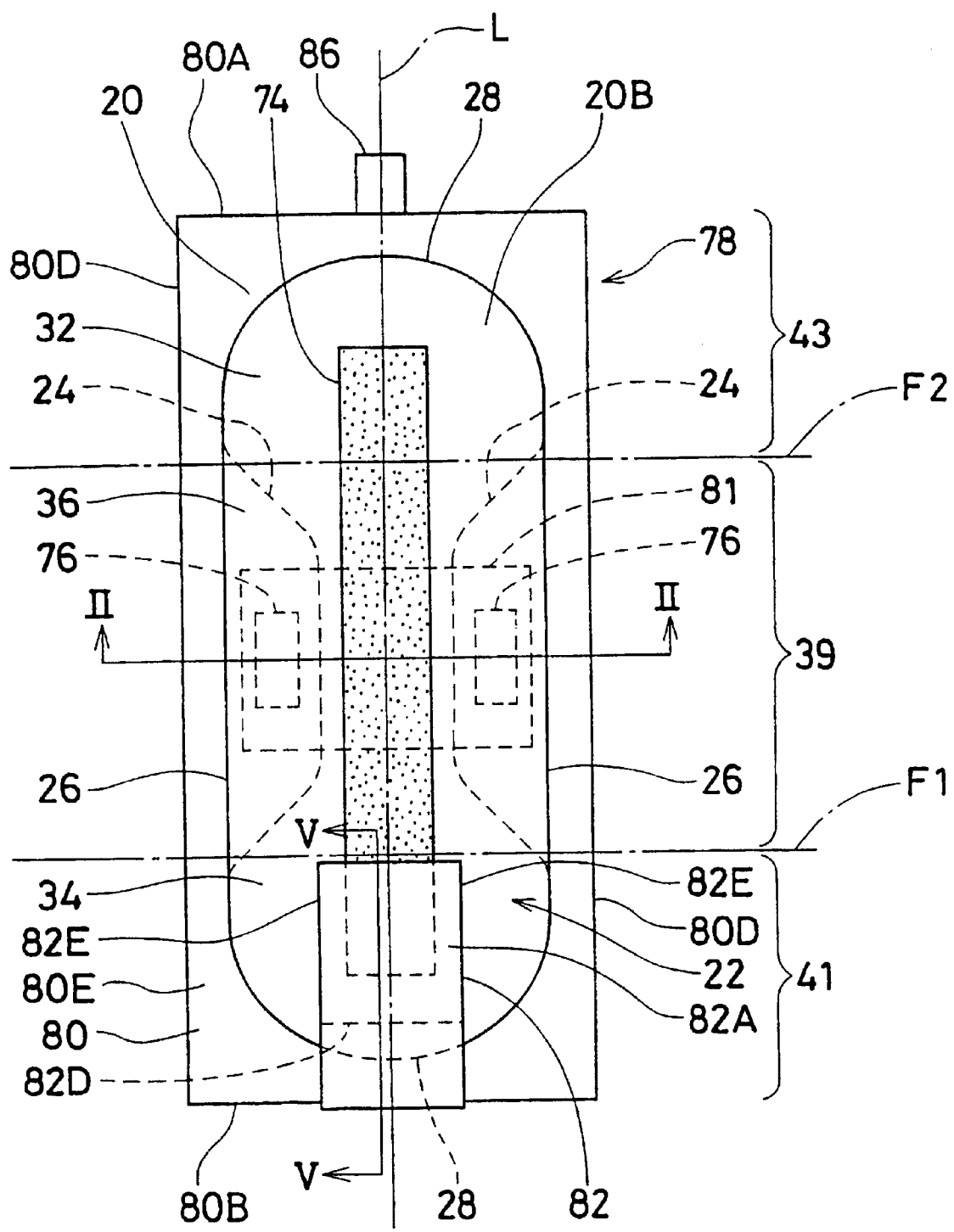
FIG. 1 is a top plan view of a preferred embodiment of the wrapper of the present invention in an opened position with a preferred sanitary napkin disposed thereon.
Figure 2:
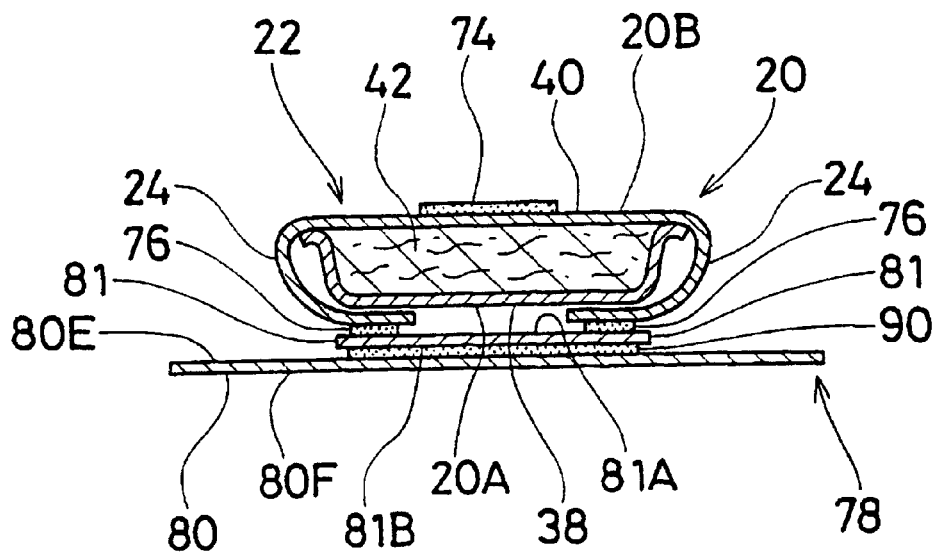
FIG. 2 is a cross-sectional view of the wrapper and the sanitary napkin taken along the line II—II of FIG. 1.

Referring now to the drawings, the present invention is disclosed in a preferred but non-limiting embodiment. As shown in FIGS. 1 and 2, the present invention includes a wrapper 78 for a disposable absorbent article, particularly a sanitary napkin 20.

Figure 3:
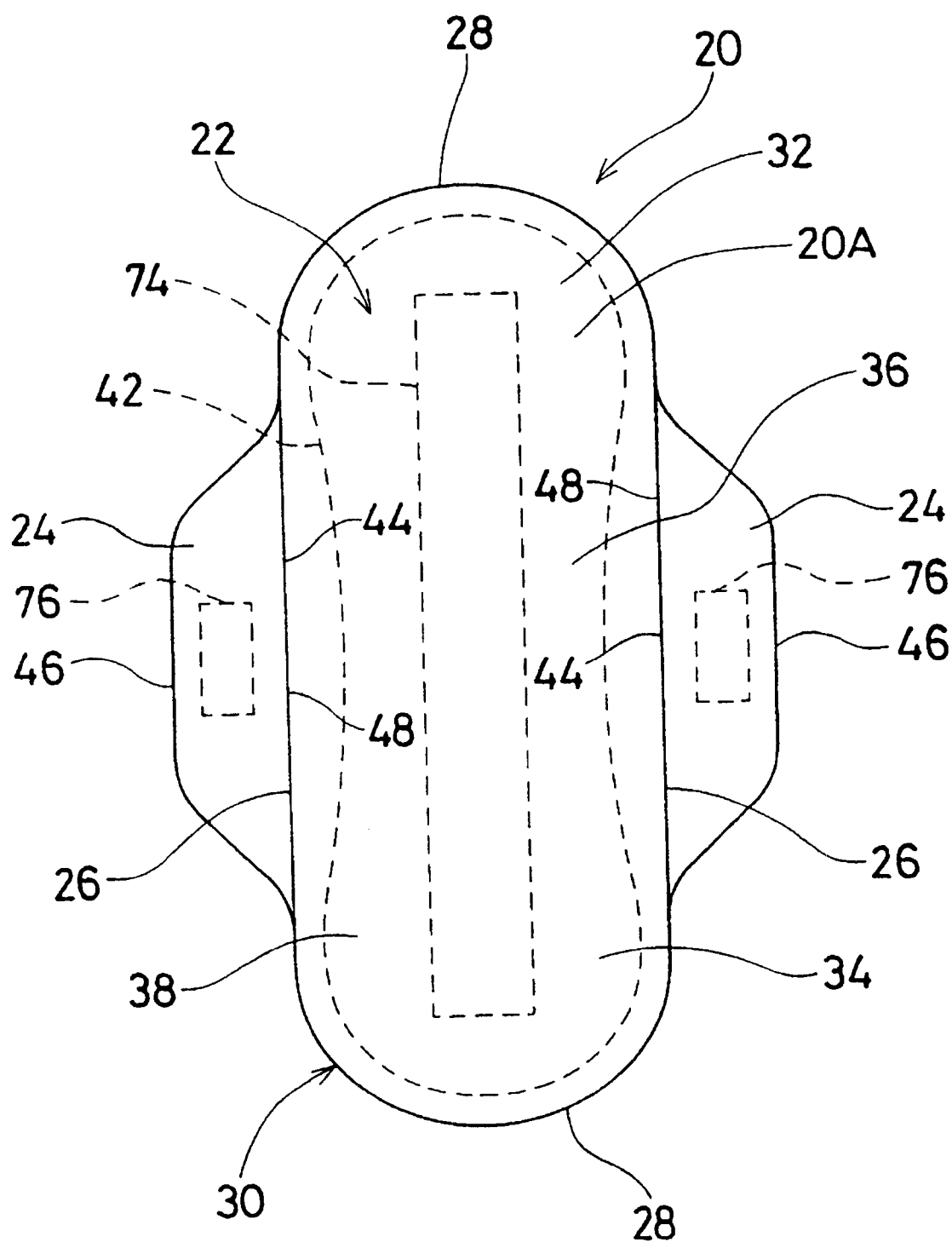
FIG. 3 is a top plan view of the sanitary napkin shown in FIG. 1 with the flaps outstretched.

The sanitary napkin 20 is used to collect vaginal discharges, such as menses, and prevent soiling of the wearer's clothing by such discharges. As shown in FIGS. 1, 2, and 3, the sanitary napkin 20 basically includes a main body portion 22. The sanitary napkin 20 may include a pair of flaps 24 which will be folded to wrap the edge of the wearer's undergarment when in use. The main body portion 22 of the sanitary napkin 20 may have a main body fastener, such as a pressure sensitive adhesive fastener thereon for fastening the main body portion 22 in the wearer's undergarment. The flaps 24 preferably each have flap fasteners thereon, such as a pressure sensitive adhesive fastener, for releasably affixing the flaps 24 of the sanitary napkin 20 in a configuration folded around the edges of the crotch of the wearer's undergarment. The wrapper 78 serves to cover and protect the flap fasteners and the body surface of the sanitary napkin 20, and is folded around the sanitary napkin 20 to provide an individual package for the sanitary napkin 20.

The sanitary napkin 20 (and the main body portion 22 thereof) has two surfaces, a liquid pervious body-contacting surface or "body surface" 20A that is intended to be worn adjacent to the body of the wearer, and a liquid impervious garment surface 20B. The sanitary napkin 20 is shown in FIG. 3 as viewed from its body surface 20A. The sanitary napkin 20 (with the other elements, such as the wrapper 78) is shown in FIG. 1 as viewed from its garment surface 20B. The sanitary napkin 20 has two centerlines, a principal longitudinal centerline L and a principal transverse centerline (not shown in FIGS). Herein "longitudinal" refers to a line, axis or direction in the plane of the sanitary napkin 20 that is generally aligned with (e.g. approximately parallel to) a vertical plane which bisects a standing wearer into left and right body halves when the sanitary napkin 20 is worn. Herein "transverse" "lateral" or "width" are interchangeable, and refer to a line, axis or direction which lies within the plane of the sanitary napkin 20 that is generally perpendicular to the longitudinal direction.

FIG. 3 shows the main body portion 22 and the flaps 24 of the sanitary napkin 20. The main body portion 22 has two spaced apart longitudinal side edges 26, two spaced apart transverse or end edges (or "ends") 28, which together form the periphery 30 of the main body portion 22. The main body portion 22 also has three sections including a central section (first section) 36, one end section (second section) 34 and the other end section (third section) 32. The first section 36 is disposed between the second section 34 and the third section 32. The second section 34 and the third section 32 extend outwardly in the longitudinal direction from the edges of the central section 36 of the main body portion 22. When the sanitary napkin 20 is individually packaged, the main body portion 22 and the wrapper 78 are folded as a unit into three regions including a first region 39, a second region 41, and a third region 43 divided by two fold axes F1 and F2 (refer to FIG. 1). The first section 36, the second section 34 and the third section 32 of the main body portion 22 generally extend in the first region 39, the second region 41 and the third region 43, respectively.

The main body portion 22 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn on Aug. 21, 1990 and Aug. 23, 1991 respectively preferably has a caliper of less than about 3 millimeters. The embodiment of the sanitary napkin 20 shown in the drawings is intended to be an example of a sanitary napkin of an intermediate thickness. The main body portion 22 of the sanitary napkin 20 may also be relatively flexible, so that it is comfortable for the wearer. It should be understood that the sanitary napkin shown is merely one embodiment, and that the wrapper of the present invention is not limited to use with absorbent articles of the type or having the specific configurations shown in the drawings.

FIG. 2 shows the individual components of the main body portion 22 of the sanitary napkin 20. The main body portion 22 of the sanitary napkin 20 preferably has at least three primary components. These include a liquid pervious topsheet 38, a liquid impervious backsheet 40, and an absorbent core 42 positioned between the topsheet 38 and the backsheet 40. The topsheet, the backsheet, and the absorbent core may be assembled in a variety of configurations known in the art (including layered or "sandwich" configurations and wrapped or "tube" configurations). Suitable materials for the components of the main body portion 22, and some of the various configurations in which such components can be assembled are described generally in, e.g., U.S. Pat. No. 4,321,924, entitled "Bordered Disposable Absorbent Article" issued to Ahr on Mar. 30, 1982; U.S. Pat. No. 4,425,130, entitled "Compound Sanitary Napkin" issued to DesMarais on Jan. 10, 1984; U.S. Pat. No. 4,950,264, entitled "Thin, Flexible Sanitary Napkin" issued to Osborn on Aug. 21, 1990; U.S. Pat. No. 5,308,346, entitled "Elasticized Sanitary Napkin" issued to Sneller, et al. on May 3, 1994, and U.S. Pat. No. 5,389,094, entitled "Absorbent Article Having Flaps and Zones of Differential Extensibility" issued to Lavash, et al. on Feb. 14, 1995. The main body portion 22 of the sanitary napkin 20 may also be formed by one or more extensible components such as those sanitary napkins, and the like described in, e.g., U.S. patent application Ser. Nos. 07/915,133 and 07/915,284, both filed Jul. 23, 1992, in the name of Osborn, et al. (PCT Publication Nos. WO 93/01785 and 93/01786, both published Feb. 4, 1993).

FIG. 2 shows a preferred embodiment of the sanitary napkin 20 assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to form portions of the periphery 30. The topsheet 38 is preferably joined to the body-facing side of the absorbent core 42 and the backsheet 40 is preferably joined to the garment-facing side of the absorbent core 42. The topsheet 38 and backsheet 40 can be joined to the absorbent core 42 in any suitable manner known in the art for this purpose, such as by an open pattern of adhesives. The portions of the topsheet 38 and backsheet 40 that extend beyond the edges of the absorbent core 42 are preferably also joined to each other. These portions of the topsheet 38 and backsheet 40 can also be joined in any suitable manner known in the art. Preferably, in the embodiment shown, these portions of the topsheet 38 and backsheet 40 are joined using adhesives over substantially the entire portions that extend beyond the edges of the absorbent core 42, and a crimp seal around the periphery 30 of the main body portion 22 where the topsheet 38 and backsheet 40 are densified by the application of pressure or heat and pressure.

The sanitary napkin 20 shown in FIG. 3, as discussed above, may have a pair of flaps 24 that are joined to the main body portion 22. The flaps 24 extend laterally outward beyond the longitudinal side edges 26 of the main body portion 22 from their proximal edges 44 to their distal edges (or "free ends") 46. The flaps 24 extend laterally outward from at least a part of the first section 36 of the main body portion 22 and majority of the flaps 24 extends in the first region 39 divided by the fold axes F1 and F2 (refer to FIG. 1).

The flaps 24 can be joined to the main body portion 22 in any suitable manner. Herein "joined" encompasses configurations in which an element is directly secured to another element by affixing the element directly to the other element, configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown in FIG. 3, the flaps 24 are integral with the main body portion 22 (that is, the flaps 24 are formed by integral extensions of the backsheet 40; alternatively, the flaps 24 may be formed by integral extensions of the topsheet 38 and the backsheet 40 which are coextensive).

In other alternative embodiments, the flaps 24 can be formed by one or more separate components that are joined to the garment-facing side of the main body portion 22. Preferably, in such a case, the flaps 24 each are formed by a separate component that is joined to the garment-facing side of the main body portion 22. In such alternative embodiments, the flaps 24 are preferably otherwise unattached to the garment-facing side of the main body portion 22 of the sanitary napkin 20 between the points where they are attached to the main body portion 22 and the longitudinal side edges 26 of the main body portion 22. The flaps 24 in these latter embodiments can be joined to the garment-facing side of the main body portion 22 by any suitable attachment mechanism. Suitable attachment mechanisms include, but are not limited to adhesives, and the like.

The places or regions on the sanitary napkin 20 where the flaps 24 are joined to (or extend from) the main body portion 22, are referred to herein as "junctures". These regions will typically be longitudinally-oriented (or "longitudinal") junctures, such as lines of juncture 48. These regions can be any of various curved or straight lines, but they are not limited to lines. Thus, the junctures may include flanges, strips, intermittent lines, and the like.

The flaps 24 may be of any configuration desired. For example, the flaps 24 are provided with zones of extensibility (not shown in FIGS.) in the front edge and the back edge of each flap 24. The zones of extensibility relieve stresses which are created in the flaps 24 by the folding of the flaps 24 around the crotch of the wearer's undergarment. The zones of extensibility thereby help eliminate bunching of the flaps 24 caused by said stresses. The zones of extensibility may be formed by pre-corrugated or "ring rolled" regions of the flaps 24 in which the corrugations define ridges and valleys that are oriented at an angle to the principal longitudinal centerline L. Suitable structures for providing the flaps 24 with zones of extensibility are described in greater detail in, e.g., U.S. Pat. No. 5,389,094 issued to Lavash, et al. and in commonly assigned copending U.S. patent application Ser. No. 08/380,769, entitled "Absorbent Article Having Flaps With Gathered Portions" filed in the name of Sue A. Mills, et al. on Jan. 30, 1995.

Figure 4:
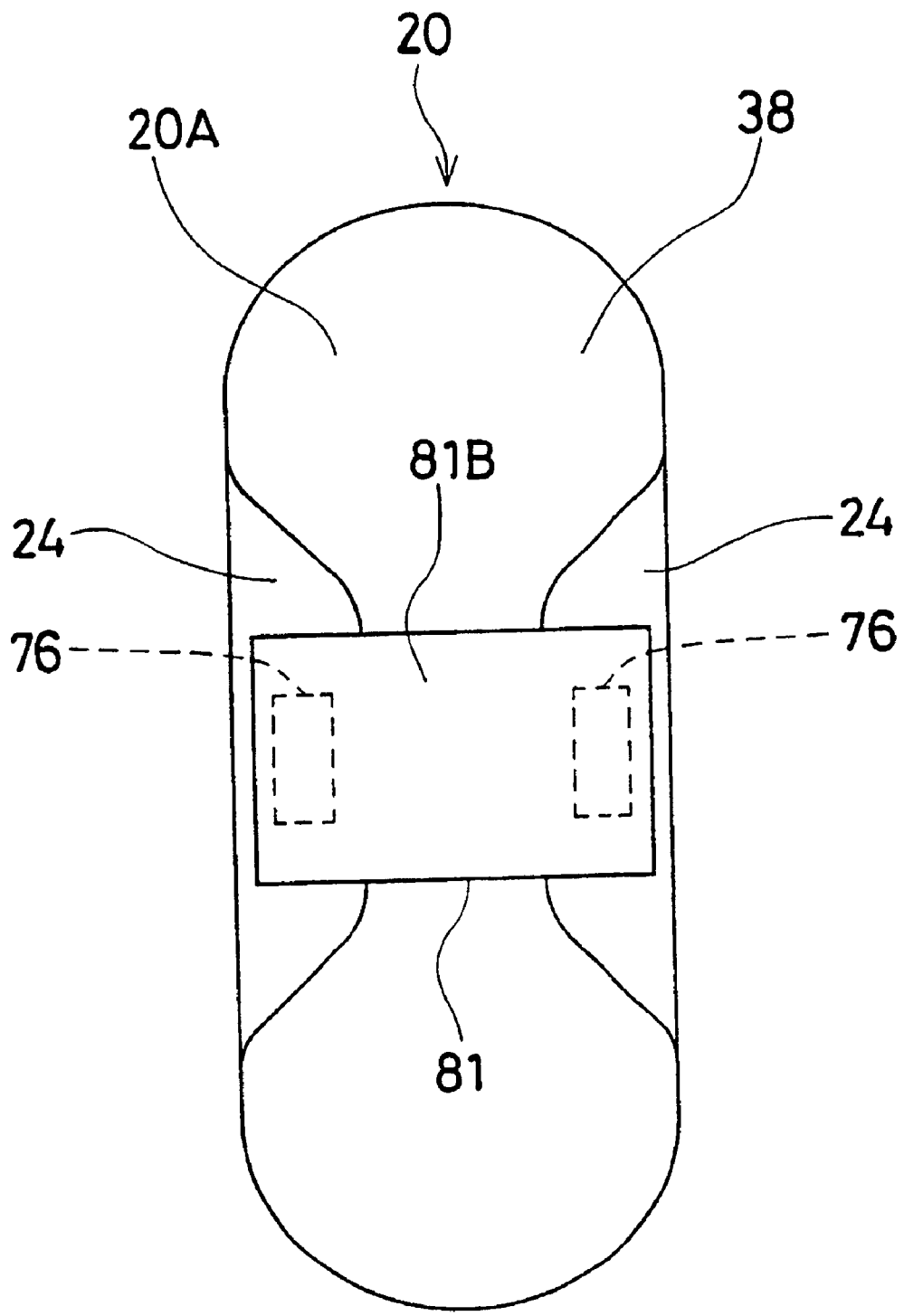
FIG. 4 is a top plan view of the sanitary napkin shown in FIG. 1 with the flaps folded over the topsheet and covered by the flap fastener cover.

The sanitary napkin 20 preferably also has fasteners for securing the sanitary napkin 20 in place in a wearer's undergarment. FIGS. 3 and 4 show a preferred arrangement of fasteners which includes a main body fastener, such as a main body adhesive 74, and flap fasteners, such as flap adhesives 76. The fasteners used with the sanitary napkin 20 are not limited to adhesive fasteners. Any suitable type of fastener known in the art can be used for this purpose. For example, the sanitary napkin 20 could be secured in place in a wearer's undergarment by mechanical fasteners, such as VELCRO®, or by a combination of adhesive and mechanical fasteners. For simplicity, however, the fasteners will be described in terms of adhesive fasteners and these fasteners are preferably pressure sensitive adhesive fasteners. Suitable pressure sensitive adhesive fasteners are described in greater detail in, e.g., U.S. Pat. No. 4,917,697 issued to Osborn, et al. on Apr. 17, 1990.

The main body adhesive 74 and the flap adhesives 76 can be provided in any suitable configuration. In the preferred embodiment shown in FIGS. 1 and 3, the main body adhesive 74 is provided in the form of one longitudinally oriented strip of adhesive that is centered about the principal longitudinal centerline L. The main body adhesive 74 may be provided in the form of two or more longitudinally oriented strips of adhesive which are disposed parallel to each other. Alternatively, the main body adhesive 74 may be provided in the form of two or more generally rectangular patches of adhesive which are disposed in the longitudinal direction at a distance. The flap adhesives 76 are provided in the form of a generally rectangular patch of adhesive on each flap 24. The main body adhesive 74 provides an adhesive attachment means for securing the main body portion 22 of the sanitary napkin 20 against the crotch portion of a panty. The flap adhesives 76 are used to assist in maintaining the flaps 24 in position after they are wrapped around the edges of the crotch portion of the panty. The flaps can be maintained in position by attaching the flaps 24 to the undergarment, or to the opposing flap. Alternatively, the flaps 24 may not be provided with the flap adhesive.

Figure 7:
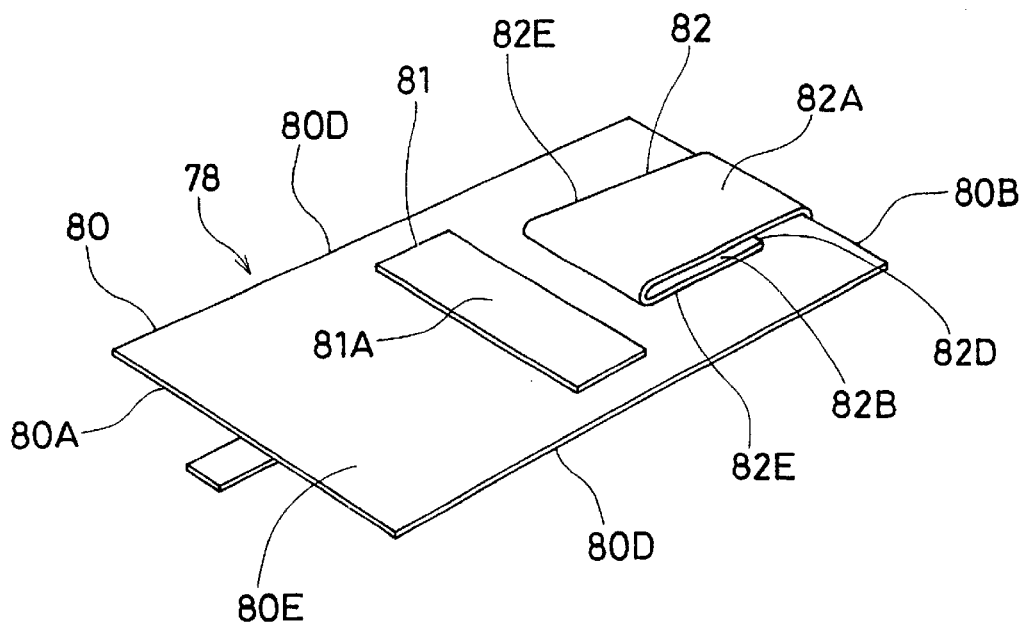
FIG. 7 is a perspective view of one preferred wrapper shown in FIG. 1.

FIGS. 1, 2 and 7 show one preferred version of the wrapper 78. The wrapper 78 may be formed by a single element or may be formed by several elements. These elements can be formed by integral portions of a single member or article, or they can be formed by separate components joined to a member or article. The elements constituting the wrapper 78 include: a main wrapper sheet 80; a main fastener cover 82; and optionally may include a flap fastener cover 81 (not shown in FIG. 2) if the flap 24 is provided and the flap adhesive 76 is provided on the flap 24.

The main wrapper sheet 80 is the portion of the wrapper 78 which will be folded around the sanitary napkin 20 to provide an individual package for the sanitary napkin 20. The main wrapper sheet 80 preferably covers the side of the body surface 20A of the sanitary napkin 20 and is releasably affixed to the sanitary napkin 20 as described hereinafter. As shown in FIGS. 1 and 7, the main wrapper sheet 80 has two surfaces, inner surface 80E and outer surface 80F (refer to FIG. 2). The inner surface 80E is the surface facing the sanitary napkin 20. The main wrapper sheet 80 preferably has dimensions that are slightly larger than those of the main body portion 22 of the sanitary napkin 20. Preferably, the main wrapper sheet 80 has longitudinal side portions 80D which extend beyond the longitudinal side edges 26 of the main body portion 22 of the sanitary napkin 20. The main wrapper sheet 80 preferably also has a first end portion 80A and a second end portion 80B which extend beyond the end edges 28 of the main body portion 22. It is recognized, however, that satisfactory protection of sanitary napkin 20 may be afforded by a wrapper which is not larger than the main body portion 22 of the sanitary napkin 20. The main wrapper sheet 80 can be made from any suitable material. The main wrapper sheet 80 is preferably manufactured from a thin flexible material which is liquid impermeable so that the wrapper 78 will be suitable for wrapping and disposing of a used sanitary napkin 20. For example, polyethylene films have been found to work well. The main wrapper sheet 80 may be formed by an opaque material, a semi-transparent material, or a transparent material. An opaque main wrapper sheet 80 offers the advantage of discreteness when used to rewrap a used/soiled sanitary for disposal. However, a semi-transparent or a transparent main wrapper sheet 80 facilitates visual placement of the sanitary napkin onto the undergarment.

Figure 5:
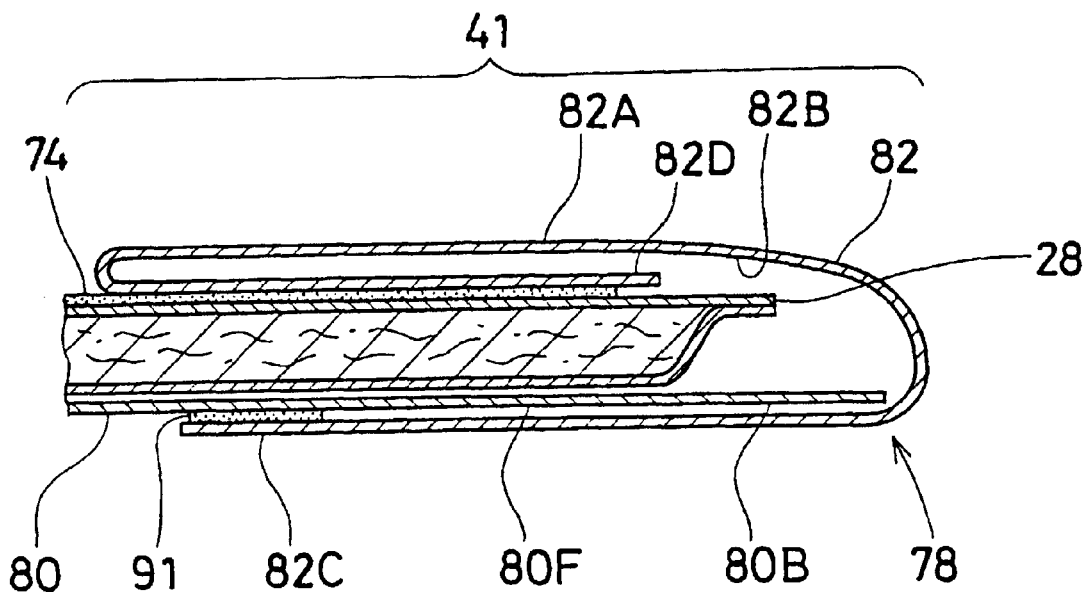
FIG. 5 is a cross-sectional view of the wrapper and the sanitary napkin taken along the line V—V of FIG. 1.

Referring to FIGS. 1, 5 and 7, the main fastener cover (or "main adhesive cover") 82 is provided to cover and protect the main body adhesive 74. The main adhesive cover 82 may be formed by a thin sheet-like element such as a paper or a plastic film. If a separate release paper is used, it can be formed by any suitable material known in the art for this purpose, such as coated papers. Suitable release papers are described in, e.g., U.S. Pat. No. 4,917,697 issued to Osborn, Apr. 17, 1990. The main adhesive cover 82 has two faces, one of which is a non-stick face (or releasable face) 82A which is capable of releasable attachment with the main fastener, and an opposite face or side 82B. When the main fasteners are formed by adhesive fasteners, the non-stick face 82A can be provided by attaching a separate release paper or element to the main adhesive cover 82 which is treated with a non-stick material, or by treating all or a portion of the main adhesive cover 82 with a non-stick coating, such as by silicone coating a portion of the main adhesive cover 82. Alternatively, if the main fasteners 74 are formed by mechanical fasteners, such as VELCRO® fasteners, the non-stick face may be provided by a nonwoven material capable of releasably engaging the mechanical fastening material. The opposite side 81B of the flap adhesive cover 81 need not have, and preferably does not have, a release coating thereon. The main adhesive cover 82 also has longitudinal side portions 82E, a fixed end portion 82C fixed proximate to the second end portion 80B of the main wrapper sheet 80, and a free end portion 82D located proximate to the end edge 28 of the sanitary napkin 20 in the second region 41 (refer to FIG. 5). The opposite face 82B of the fixed end portion 82C faces the outer surface 80F proximate to the second end portion 80B and is joined thereto by any suitable means such as adhesive 91. The free end portion 82D is folded such that the non-stick face 82A faces the main body adhesive 74 in the second region 41.

The main adhesive cover 82 can be of any suitable size and shape, though the figures depict a main adhesive cover 82 which is only of sufficient width and length to cover and protect the main body adhesive 74. Preferably, the lateral width of the main adhesive cover 82 is narrower than that of the main wrapper sheet 80. Thereby, the longitudinal side portions 82E do not extend into a frangible sealed region (explained later) of the longitudinal side portions 80D of the main wrapper sheet 80 which is to complete the individual packaging.

Figure 8:
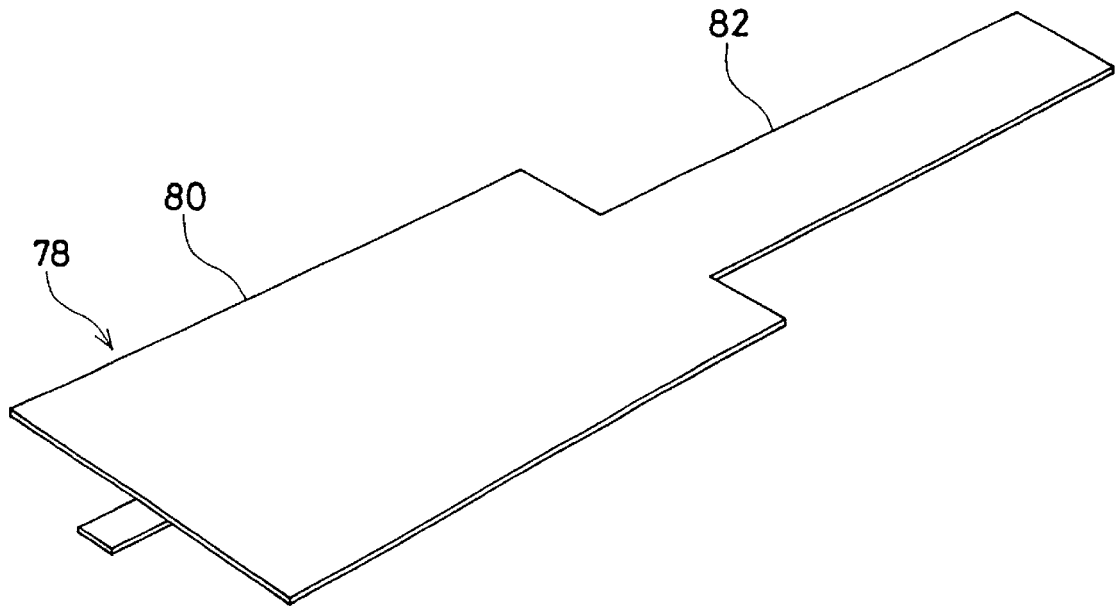
FIG. 8 is a perspective view of an alternative embodiment of the wrapper.

FIG. 8 shows an alternative embodiment of the wrapper 78 having a main wrapper sheet 80 and a main adhesive cover 82. In the embodiment shown in FIG. 8, instead of being a separate component of the main wrapper sheet 80, the main adhesive cover 82 is an integral portion of the main wrapper sheet 80.

Figure 6:
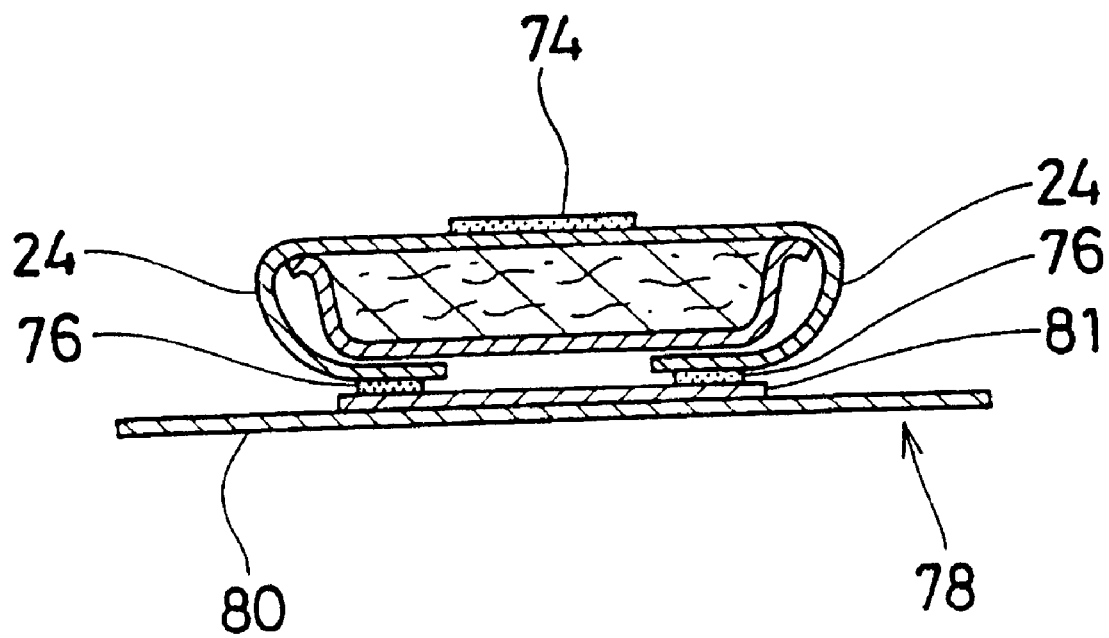
FIG. 6 is a cross-sectional view of an alternative embodiment of the wrapper and the sanitary napkin.

The flap fastener cover (or "flap adhesive cover") 81 (if provided) covers and protects the flap adhesives 76 in a packaged configuration of the sanitary napkin 20 by the wrapper 78. It also maintains the flaps 24 in position folded over the topsheet 38. FIG. 4 shows one example of the flap adhesive cover 81 formed by a separate flap adhesive cover sheet before the flap adhesive cover 81 is joined to the main wrapper sheet 80. Such a release paper 81 can be laminated to the inner surface 80E of the main wrapper sheet 80 as shown in FIG. 2 before or after the flap adhesive cover 81 is releasably affixed to the flap adhesives 76. The flap adhesive cover 81 has two faces, one of which is a non-stick face (or releasable face) 81A which is capable of releasable attachment with the flap fasteners, and an opposite face or side 81B. As shown in FIG. 2, the non-stick face 81A is disposed to face the flap adhesives 76 such that it will be able to releasably adhere to the flap adhesive 76. The opposite side 81B faces away from the flap adhesives 76 as shown in FIGS. 2 and 4. The opposite side 81B is joined to the inner surface 80E of the main wrapper sheet 80 by any suitable means such as adhesive layer 90 as shown in FIG. 2. As the main wrapper sheet 80 is removed from the sanitary napkin 20, the flap adhesive cover 81 is removed from the flap adhesives 76 of the sanitary napkin 20 while remaining on the main wrapper sheet 80. The non-stick surface 81A may be formed by the same material or element as the non-stick face 82A of the main adhesive cover 82. The opposite side 81B may have, or may not have, a release coating thereon. Alternatively, as shown in FIG. 6, the flap adhesive cover 81 may be provided on the main wrapper sheet 80 as a release coating. The flap adhesives 76 may be releasably affixed to the release coating 81. If a release coating is used, the coating can be applied directly to the inner surface 80E of the main wrapper sheet 80. Such a coating can be formed by any material known in the art for this purpose, with silicone coatings being preferred. If a coating is used, the coating 81 may be provided by coating only that zone of the main wrapper sheet 80 which will substantially contact the flap adhesives 76. Alternatively, the entire inner surface 80E of the main wrapper sheet 80 may be coated. Coating the entire inner surface of a wrapper is disclosed in, e.g., U.S. Pat. No. 5,181,610 entitled "Flexible Container with Nonstick Interior" which issued to Quick et al. on Jan. 26, 1993.

The flap adhesive cover 81 can be of any suitable size and shape, though the figures depict a flap adhesive cover 81 which is only of sufficient width and length to cover and protect the flap adhesives 76.

The wrapper 78 preferably also may include an optional package fastener 86 for retaining the package formed by folding the wrapper and sanitary napkin in its folded configuration. The package fastener 86 is preferably both releasably attachable to the package and resealable. The package fastener 86 may be formed by any releasably attachable and resealable fastener known in the art, such as spots or patches of adhesive, tapes, and mechanical fasteners. A package fastener with a pressure sensitive adhesive located thereon has been found to work well. The package fastener 86 can be disposed at any suitable location on the wrapper 78. In the embodiment shown in FIG. 1, the package fastener 86 is preferably positioned at opposing first end portion 80A of the main wrapper sheet 80.

Figure 9:
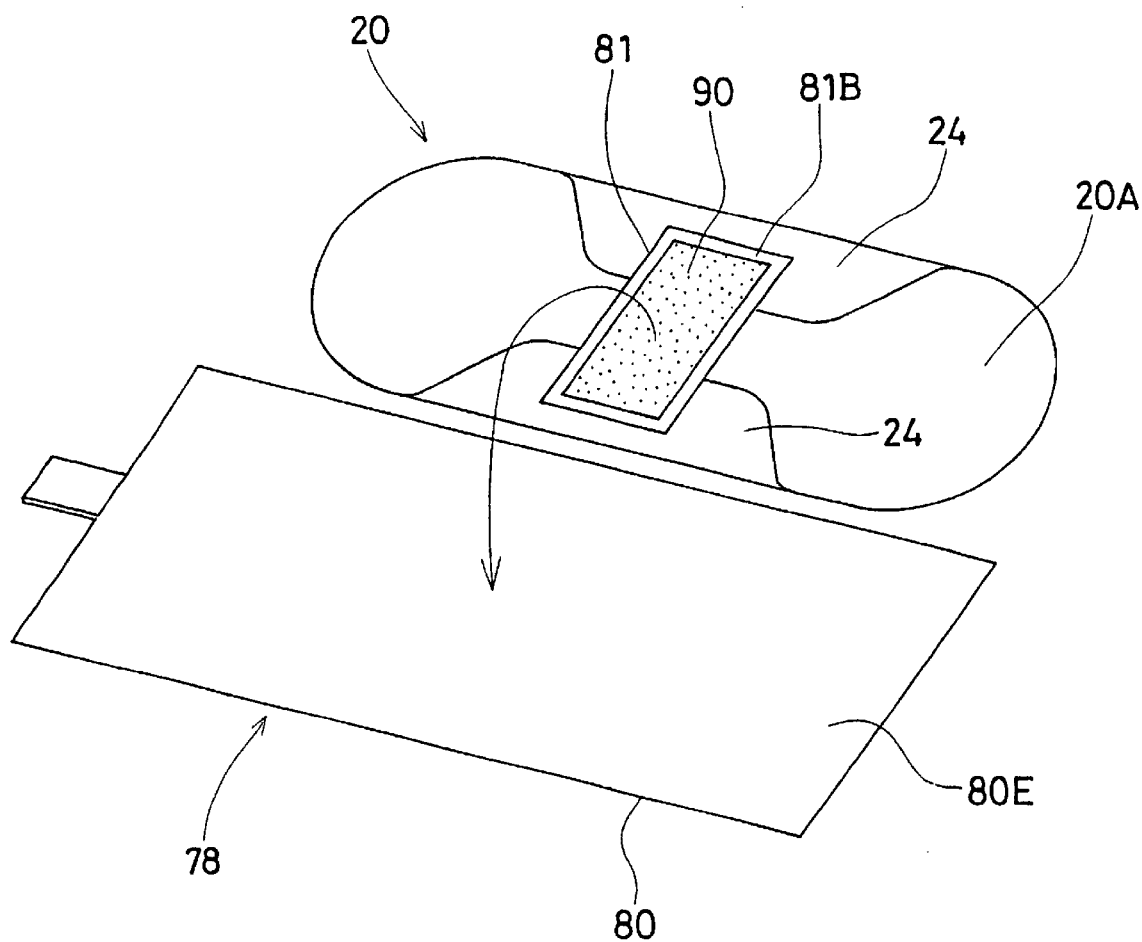
FIG. 9 is a first schematical perspective view showing a packaging process of the sanitary napkin by the wrapper.
Figure 10:
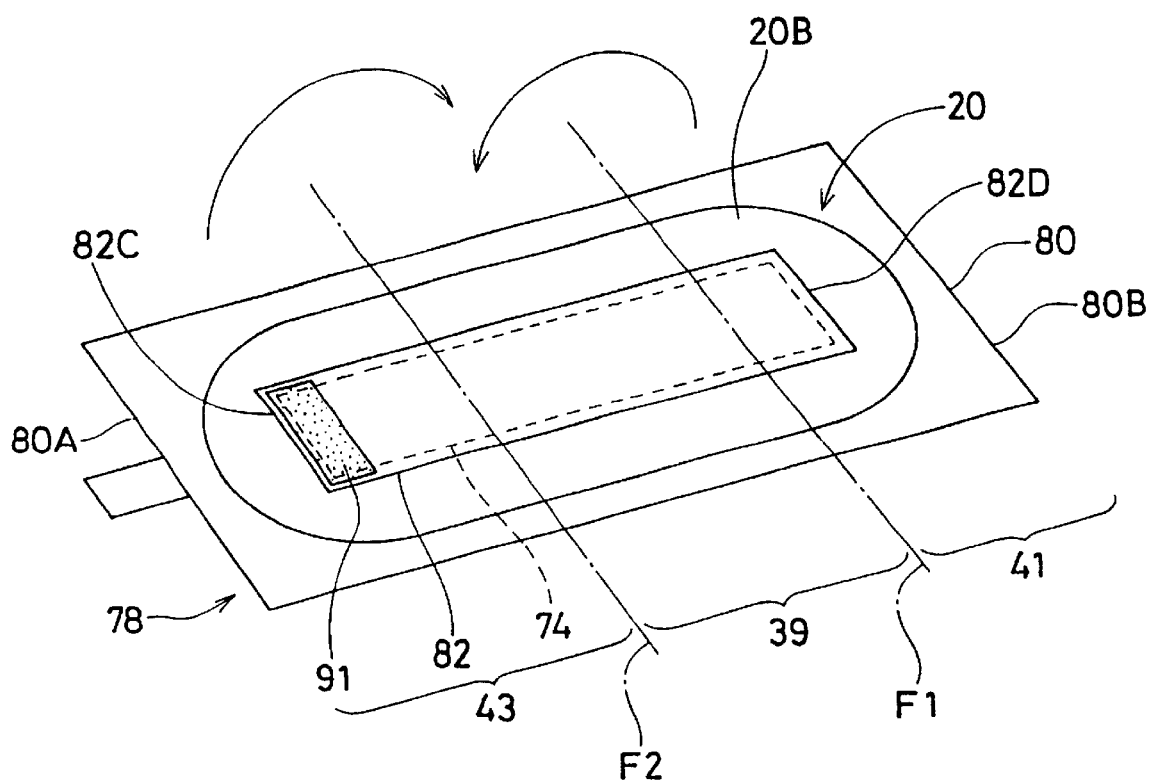
FIG. 10 is a second schematical perspective view showing a packaging process of the sanitary napkin by the wrapper.
Figure 11:
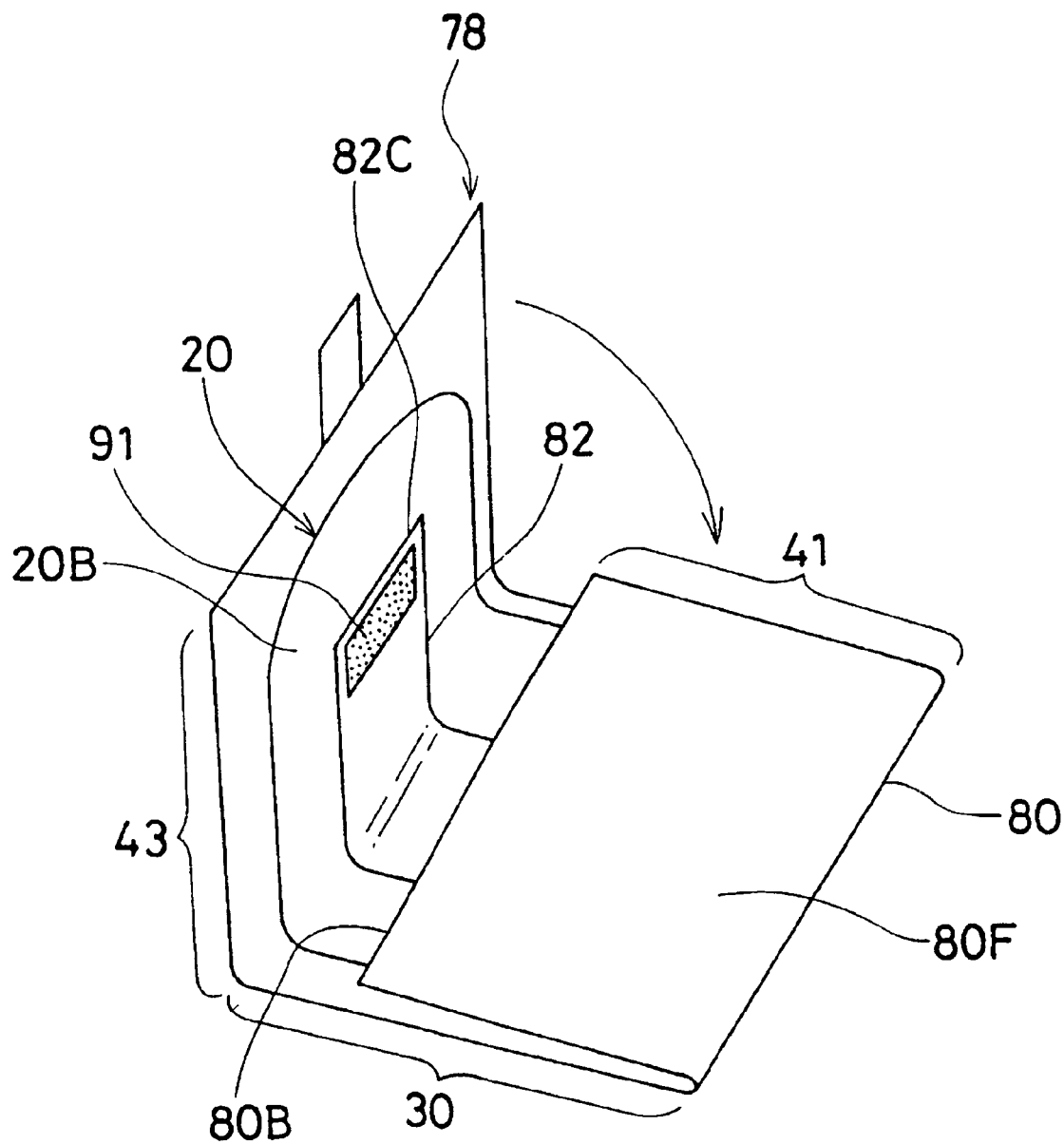
FIG. 11 is a third schematical perspective view showing a packaging process of the sanitary napkin by the wrapper.

FIGS. 9–11 show one example of a process for packaging the sanitary napkin 20 in the wrapper 78. In this embodiment, the flap adhesive cover 81 is provided and is a separate flap adhesive cover sheet. The main adhesive cover 82 is a separate single sheet. Prior to packaging the sanitary napkin 20 in the wrapper 78, the first flaps 24 are folded onto the topsheet 38 (i.e., body surface 20A). Folding the flaps 24 in the configuration shown in FIG. 6 exposes the patches of adhesive 76 disposed on the garment surface 20B of flaps 24 and causes the flaps 24 to cover at least a portion of the topsheet 38. The folded left and right flaps 24 are connected to each other by the flap adhesive cover 81. The flap adhesive cover 81 covers the flap adhesives 76 (not shown in FIGS. 9–11) and maintains the flaps 24 in position folded over the topsheet 38. The adhesive layer 90 is provided on the opposite side 81B of the flap adhesive cover 81. As shown in FIGS. 9 and 10, the sanitary napkin 20 is placed on top of the main wrapper sheet 80 (i.e., the inner surface 80E) such that the opposite side 81 B of the flap adhesive cover 81 faces the inner surface 80E of the main wrapper sheet 80. Thereby the flap adhesive cover 81 is joined to the main wrapper sheet 80 by the adhesive layer 90. The body surface 20A faces the inner surface 80E of the main wrapper sheet 80. Disposing the body surface 20A of the sanitary napkin 20 facing the main wrapper sheet 80 can be considered to provide protection to prevent the topsheet 38 from becoming soiled prior to use. Alternatively, the flap adhesive cover 81 may be joined to the inner surface 80E of the main wrapper sheet 80 before the flap adhesive cover 81 is releasably affixed to the flap adhesives 76. In this case, the sanitary napkin 20 is placed on top of the main wrapper sheet 80 such that the flap adhesives 76 lies over the flap adhesive cover 81 on the main wrapper sheet 80.

The main body adhesive 74 on the garment surface 20B is covered by the main adhesive cover 82 as shown in FIG. 10. As shown, in the configuration where the main adhesive cover 82 has not yet been joined to the main wrapper sheet 80, the fixed end portion 80A of the main adhesive cover 82 is located proximate to the first end portion 80A of the main wrapper sheet 80. The free end portion 82D is located proximate to the second end portion 80B of the main wrapper sheet 80. The fixed end portion 82C is located in the third region 43 and the free end portion 82D is located in the second region 41. The main adhesive cover 82 may be releasably affixed to the main body adhesive 74 before or after the sanitary napkin 20 is placed on the main wrapper sheet 80. The adhesive layer 91 is provided on the opposite side 82B of the main adhesive cover 82 proximate to the first end portion 82C of the main adhesive cover 82. The adhesive layer 91 may be applied thereto anytime before the sanitary napkin 20 and the wrapper 78 are folded as a unit.

Figure 12:
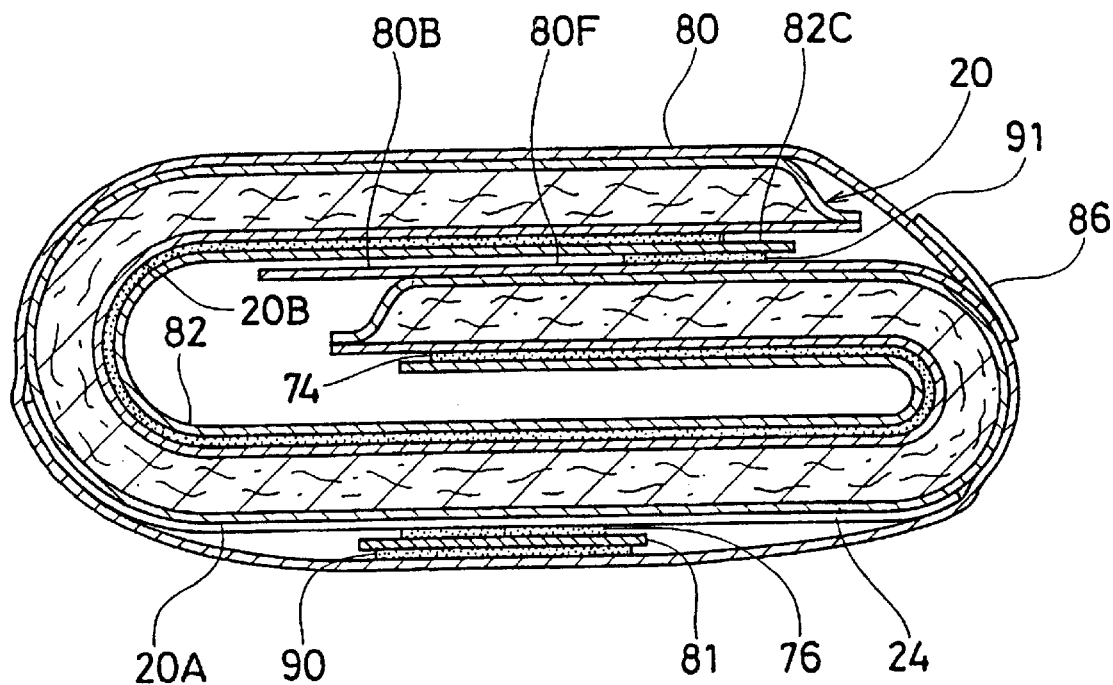
FIG. 12 is a cross-sectional view (taken along the longitudinal centerline) of the sanitary napkin and the wrapper folded by the processes shown in FIGS. 9–11.
Figure 13:
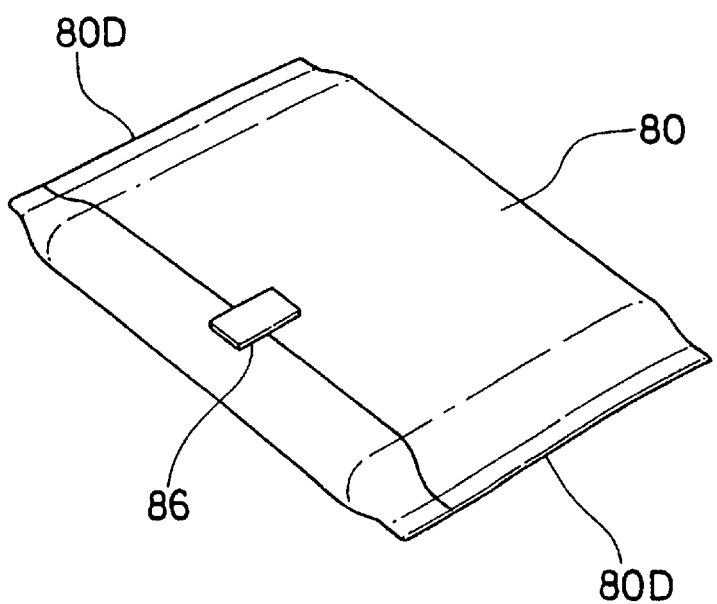
FIG. 13 is a perspective view of an embodiment of individually packaged absorbent article of the present invention assembled by utilizing the processes shown in FIGS. 9–11.

After disposing the sanitary napkin 20 on the main wrapper sheet 80 as shown in FIG. 10, the sanitary napkin 20 will then preferably be folded as a unit, together with the wrapper 78 including the main wrapper sheet 80, the flap adhesive cover 81, and the main adhesive cover 82, into three regions that are defined by the fold axes F1 and F2. The fold axes F1 and F2 will divide both the sanitary napkin 20 and the wrapper 78 into three regions including the first region 39, the second region 41 and the third region 43. As shown in FIG. 10, the central region (the first region) 39 lies between preferred fold axes F1 and F2. The second and third regions 41 and 43 lie longitudinally outboard of the fold axes F1 and F2. As described above, the main body portion 22 is also separated at the fold axes F1 and F2 into three sections including the first section 36, the second section 34, and the third section 32. Each section 36, 34 and 32 generally extends in each region 39, 41 and 43 respectively (refer to FIG. 1 as well). As shown in FIG. 10, the sanitary napkin 20 and the wrapper 78 of the second region 41 is folded as a unit toward the sanitary napkin 20 of the first region 39 such that the garment surface 20B of the sanitary napkin 20 is oriented inwardly with respect to the folded unit and the main wrapper sheet 80 is oriented outwardly with respect to the folded unit (refer to FIG. 11 as well). Then, the sanitary napkin 20 and the wrapper 78 of the third region 43 is folded onto the wrapper 78 (i.e., the main wrapper sheet 80) of the second region 41 such that the garment surface 20B of the third region 43 faces the outer surface 80F of the main wrapper sheet 80. Because of the adhesive layer 91 disposed on the main adhesive cover 82, the fixed end portion 82C of the main adhesive cover 82 joins to the outer surface 80F proximate to the second end portion 80B of the main wrapper sheet 80 as shown in FIG. 12. In the folded configuration, the body surface 20A of the sanitary napkin 20 is covered by the main wrapper sheet 80. In addition, the garment surface 20B is oriented inwardly with respect to the folded unit of the sanitary napkin 20 and the wrapper 78. Preferably, in the folded configuration, the sanitary napkin 20 is fully wrapped by the main wrapper sheet 80 and is not exposed outside the main wrapper sheet 80 (i.e., neither the body surface 20A and the garment surface 20B are exposed outside the main wrapper sheet 80). Alternatively, the sanitary napkin 20 may be folded together with the wrapper 78 into two regions that are divided by one fold axis. In such a case, the sanitary napkin 20 and the wrapper 78 are folded about the axis such that a part of the sanitary napkin 20 in one region faces a part of the sanitary napkin 20 in the other region. In this configuration, the garment surface of the sanitary napkin 20 is oriented inwardly to the folded unit of the sanitary napkin and the wrapper. Preferably, to complete the individual packaging of the sanitary napkin 20 in the wrapper 78, each longitudinal side portion 80D of the main wrapper sheet 80 is then frangibly sealed as shown in FIG. 13 after the sanitary napkin 20 and the wrapper 78 are in the folded configuration. The frangible sealing of the longitudinal side portions 80D of the main wrapper sheet 80 can be accomplished by any suitable sealing technique. By way of example only, the longitudinal side portions 80D may be heat sealed, glued, or ultrasonically bonded. The entire sanitary napkin 20 is thereby protected until the main wrapper sheet 80 is opened. Suitable methods for frangibly sealing the longitudinal side portions are described in, e.g., U.S. Pat. No. 4,556,146 issued to Swanson. FIG. 13 depicts the package for the sanitary napkin formed by folding the wrapper 78 and sanitary napkin 20 in one preferred configuration for shipment, sale, and convenient carrying by the wearer.

Figure 14:
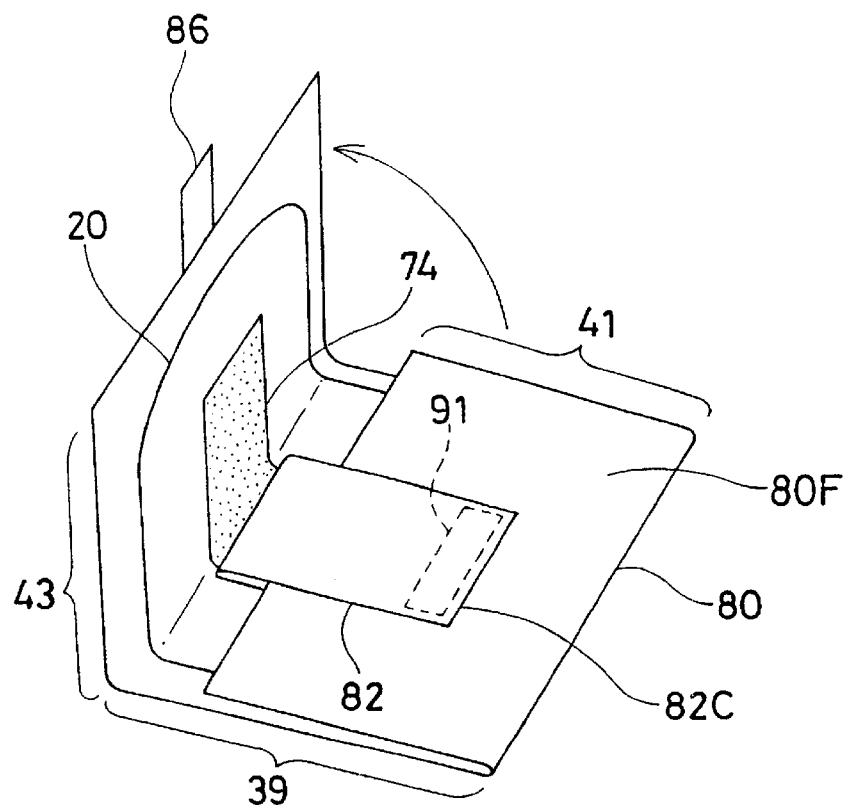
FIG. 14 is a first schematical perspective view showing an opening process of the individually packaged sanitary napkin assembled by utilizing the processes shown in FIGS. 9–11.
Figure 15:
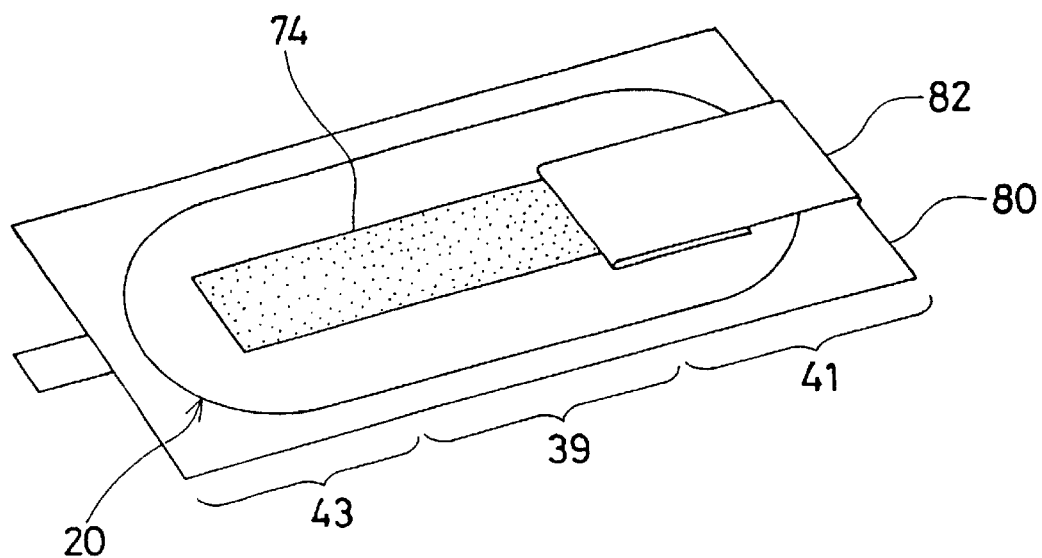
FIG. 15 is a second schematical perspective view showing an opening process of the individually packaged sanitary napkin assembled by utilizing the processes shown in FIGS. 9–11.
Figure 16:
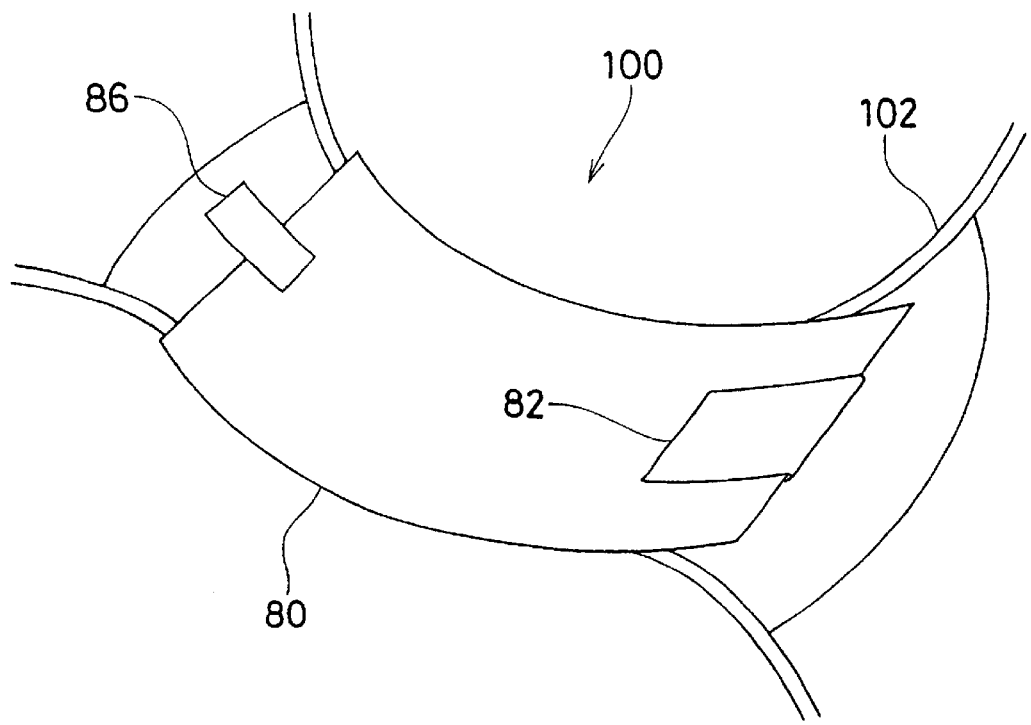
FIG. 16 is a first schematical perspective view showing an applying process of the sanitary napkin to the undergarment assembled by utilizing the processes shown in FIGS. 9–11.
Figure 17:
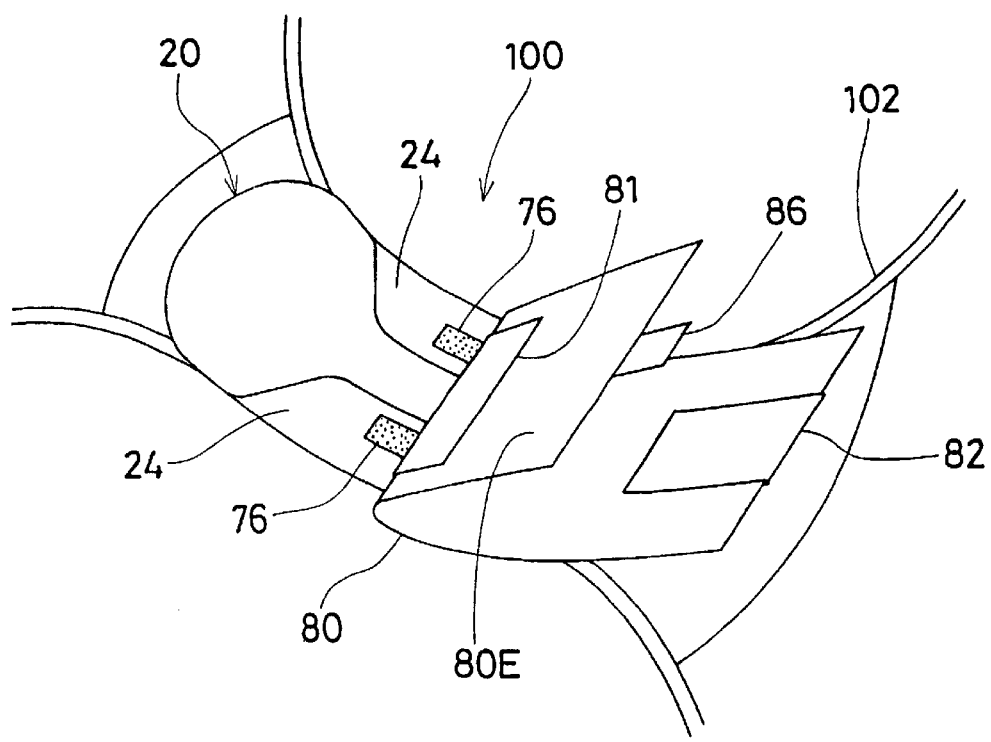
FIG. 17 is a second schematical perspective view showing an applying process of the sanitary napkin to the undergarment assembled by utilizing the processes shown in FIGS. 9–11.
Figure 18:
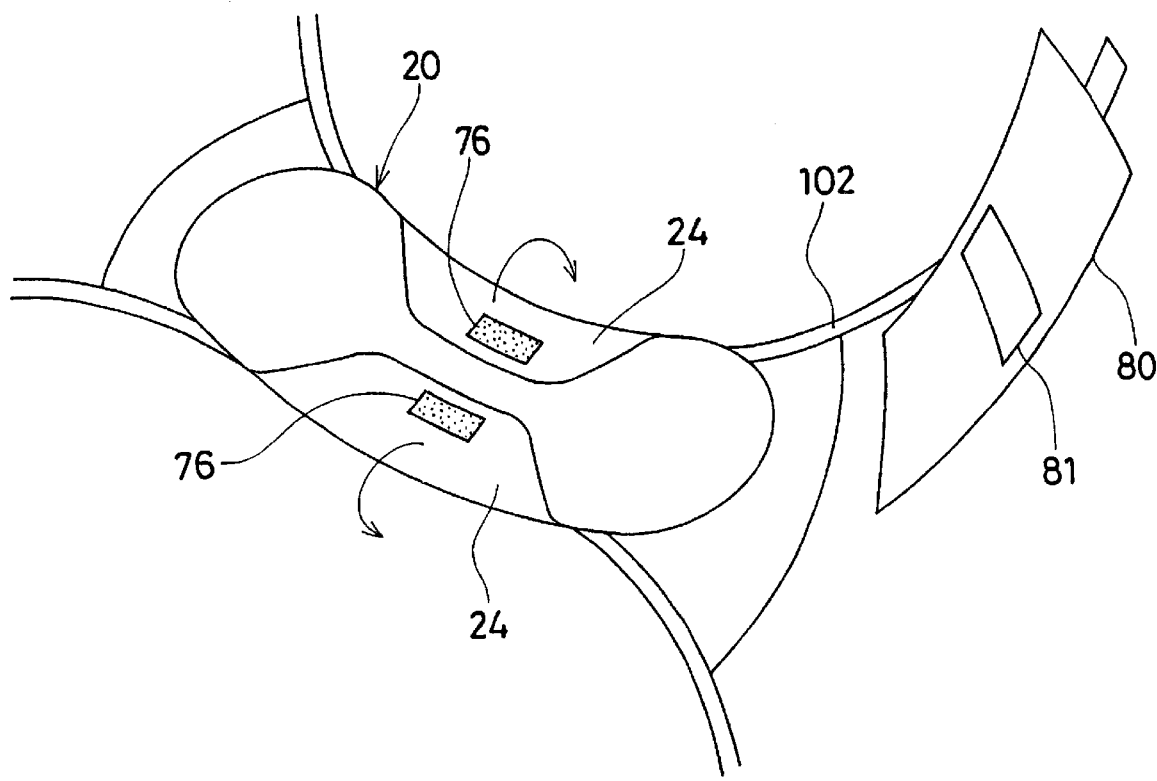
FIG. 18 is a third schematical perspective view showing an applying process of the sanitary napkin to the undergarment assembled by utilizing the processes shown in FIGS. 9–11.

The wearer will ordinarily carry the individually packaged sanitary napkin in the form depicted in FIG. 13. The individually packaged sanitary napkin may be opened by peeling the package fastener 86 from the wrapper 78 and breaking the frangible seals along the longitudinal side portions 80D of the main wrapper sheet 80 such that the sanitary napkin 20 of the third region 43 is opened from the main wrapper sheet 80 of the second region 41 as shown in FIG. 14. Because the fixed end portion 82C is joined to the outer surface 80F of the main wrapper sheet 80, the fixed end portion 82C remains with the main wrapper sheet 80. Thereby a part of the main body adhesive 74 located in the third region 43 is automatically exposed coincidentally as the third region 43 is opened from the second region 41. Then the second region 41 is opened from the first region 39 in order to further expose the main body adhesive 74 located in the first region 39 as shown in FIG. 15. Thus, by opening the wrapped sanitary napkin, at least a part of the main body adhesive 74 is exposed so that it will be able to attach to the crotch region of the undergarment, while the body surface 20A (not shown in FIG. 15) of the sanitary napkin 20 is still covered by the main wrapper sheet 80 to protect it from contamination. As shown in FIG. 16, the sanitary napkin 20, whose body surface 20A (not shown) is covered by the main wrapper sheet 80, is placed on the crotch portion 100 of the undergarment 102 such that the main adhesive 74 (now exposed) faces the inside of the crotch region 100. This can be done without touching the body surface 20A (which will subsequently directly touch the wearer's body during use) because the body surface 20A is still covered by the main wrapper sheet 80. In addition, the first flap adhesive 76 does not inadvertently stick to the hands of the wearer or a portion of the sanitary napkin 20 because the first flap adhesive 76 is covered by the main wrapper sheet 80. In this embodiment, during application process of the sanitary napkin 20 to the undergarment 102, the main wrapper sheet 80 does not easily detach from the sanitary napkin 20 because the main wrapper sheet 80 and the sanitary napkin 20 are affixed to each other by means of the flap adhesive 76. Although the main wrapper sheet 80 is releasably affixed to the sanitary napkin 20, it can be controlled such that the main wrapper sheet 80 does not easily detach from the sanitary napkin 20 during application process of the sanitary napkin 20 to the undergarment. The configuration (how large the flap fasteners are) and/or adhering strength of the flap adhesive 76 may be independently chosen to control it. Adjustment of the configuration (e.g., bigger area of adhesive) and/or adhering strength (e.g., higher average adhering strength of adhesive) has no impact to wearer's skin comfortableness during the use of the sanitary napkin 20. As the configuration of the flap adhesive 76 becomes bigger and/or adhering strength becomes higher, the main wrapper sheet 80 becomes tends not to detach from the absorbent article. Further, in this embodiment, because the flap adhesive 76 is utilized to releasably affix the main wrapper sheet 80 to the sanitary napkin 20, no additional means to affix the main wrapper sheet 80 and the sanitary napkin 20, such as adhesives provided on the topsheet which may cause skin problem or cause the wearer to feel stickiness, is necessary. Because the body surface 20A (not shown in FIG. 16) is covered by the main wrapper sheet 80, the body surface 20A is protected from contamination during the application process of the sanitary napkin to the undergarment. Therefore, the wearer may push the side of the main wrapper sheet 80 toward the undergarment 102 to secure the main adhesive 74 to the crotch portion 100. Then the wearer pulls the package fastener 86 to remove the main wrapper sheet 80 from the sanitary napkin 20 which is secured to the crotch portion 100 of the undergarment 102. As shown in FIG. 17, as the main wrapper sheet 80 is removed, the flap adhesive cover 81 which is joined to the inner surface 80E of the main wrapper sheet 80 is removed from the flap adhesive 76. The wearer further pulls the main wrapper sheet 80 to remove the main wrapper sheet 80 from the sanitary napkin 20 as shown in FIG. 18. Because the fixed end portion 82C of the main adhesive cover 82 is joined to the outer surface 80F of the main wrapper sheet 80 proximate to the second end portion 80B of the second region 41, the wearer is able to peel the main adhesive cover 82 together with the main wrapper sheet 80 from the main body adhesive 74 without feeling shear force therebetween. Thus, after placing the sanitary napkin 20 with the main wrapper sheet 80 against the crotch region 100 (FIG. 16), removal of the main wrapper sheet 80 and the main adhesive cover 82 can be done in a single motion of pulling a part of main wrapper sheet 80. After the completion of removal, the wearer flips over the flap 24 toward the outside surface of the undergarment. Once the sanitary napkin is removed from the wrapper 78 and installed in the wearer's undergarment, the wearer may fold the wrapper 78, secure the wrapper 78 in its folded orientation by reattaching resealable package fastener 86 to wrapper 78. The wearer may then store the folded wrapper 78 for rewrapping and disposing of the used sanitary napkin. The wearer need not worry about collecting and disposing of loose flap adhesive cover 81 and main adhesive cover 82 since the flap adhesive cover 81 and the main adhesive cover 82 are joined to the main wrapper sheet 80. Therefore, the present invention provides the wearer with a clean sanitary napkin 20 which is easily installed while keeping the body surface hygienic and without extra pieces of waste which must be collected.

Various alternative embodiments of the present invention are possible. For example in the embodiment explained above, instead of having the flaps 24, the sanitary napkin 20 could be formed by only the main body portion without the flaps 24. In such a case, a releasable joint means may be provided between the body surface 20A of the sanitary napkin 20 and the main wrapper sheet 80. Such releasable joint means may be formed by any suitable means. Preferably, the joint means is formed by a means which does not have a negative impact to the wearer's skin, but has adhering strength sufficient to affix the main wrapper sheet 80 to the body surface 20A such that the main wrapper sheet 80 does not detach from the main body portion 22 even during application process of the sanitary napkin 20. If the main wrapper sheet 80 and the body surface 20A (i.e., topsheet 38) are formed by a thermoplastic material, they may be fused to each other at one or more small spots. However, the number of the fused spots and the area of the fused spots are preferably chosen not to give the wearer stiffness feeling due to the fused area while the main wrapper sheet 80 is readily released from the body surface 20A. Although it is less preferred, adhesive may be used to join the main wrapper sheet 80 and the body surface 20A. The sanitary napkin 20 may have another additional pair of flaps. The additional flaps extend laterally outward beyond the longitudinal side edges 26 of the main body portion 22. The additional flaps are positioned proximate to one end edge 28 of the main body portion 22 and apart from the flaps 24 in the longitudinal direction of the main body portion 22. The additional flaps preferably each have additional fasteners thereon, such as a pressure sensitive adhesive fastener, for releasably affixing the additional flaps of the sanitary napkin 20 in a configuration staying widespread in a back region of the inside of a wearer's undergarment. The additional flap adhesives are used to assist in maintaining the additional flaps in position after they are rendered widespread in a back region of the inside of the panty. In order to cover the additional flap adhesive, an additional flap adhesive cover may be provided. The additional flap adhesive cover may be formed by the same material/shape as the flap adhesive cover 81 of the flap adhesive 76 and is joined to the inner surface 80E of the main wrapper sheet.

It is to be recognized that the foregoing detailed description of the preferred embodiment of the present invention is given merely by way of illustration, and that numerous modifications and variations may become apparent to those skilled in the art without departing from the spirit and scope of the invention. Therefore, the scope of the present invention is to be determined by reference to the appended claims.

What is claimed is:

1. An individually packaged absorbent article comprising:

(a) an absorbent article extending in a longitudinal direction and including a main body portion having a pair of longitudinal side edges, a pair of end edges, a garment surface, and a body surface, wherein the garment surface of the main body portion has a main fastener, (b) a wrapper for the absorbent article, the wrapper having a main wrapper sheet and a main fastener cover, wherein (c) the body surface of the main body portion is disposed to face the main wrapper sheet, and the main fastener of the main body portion is covered by the main fastener cover, wherein the main fastener cover is joined to the main wrapper sheet, and (d) the main body portion and the wrapper are folded as a unit at least about one transverse axis such that the garment surface is oriented inwardly with respect to the folded unit, wherein at least a part of the main fastener is exposed when the wrapper is opened.

2. The absorbent article of claim 1 wherein:

the main wrapper sheet has a pair of longitudinal side portions, a first end portion, and a second end portion, the main fastener cover has a pair of longitudinal side portions, a fixed end portion, and a free end portion, the fixed end portion located proximate to the second end portion of the main wrapper sheet in the folded configuration, wherein the fixed end portion is joined to the second end portion of the main wrapper sheet.

3. The absorbent article of claim 2 wherein:

the main body portion and the wrapper have two transverse axes and three regions, wherein the two axes have a first axis and a second axis, and the three regions have a first region, a second region, and a third region, wherein the first region and the second region are separated by the first axis, and the first region and the third region are separated by the second axis, wherein the main body portion and the wrapper are folded along the first axis such that the main body portion of the second region superposes on the main body portion of the first region, and folded along the second axis such that the main body portion of the third region superposes on the main wrapper sheet of the second region.

4. The absorbent article of claim 3 wherein the fixed end portion of the main fastener cover is joined to the second end portion of the main wrapper sheet of the second region.

5. The absorbent article of claim 4 wherein the main fastener cover extends at least in a part of the third region, wherein the fixed end portion of the main fastener cover is joined to the second end portion of the main wrapper sheet of the second region.

6. The absorbent article of claim 5 wherein the main fastener cover extends along the first region, the second region, and the third region.

7. The absorbent article of claim 1 wherein the main fastener cover is formed by a separate element from the main wrapper sheet.

8. The absorbent article of claim 1 wherein the absorbent article has a pair of flaps joined to the main body portion and extending laterally outward beyond the longitudinal side edges of the main body portion, the garment surface of the flap has a flap fastener.

9. The absorbent article of claim 8 wherein the flaps are folded over the body surface of the main body portion to expose the flap fasteners, wherein the flap fastener is releasably affixed to the main wrapper sheet.

10. The absorbent article of claim 9 wherein the wrapper includes a flap fastener cover provided on the main wrapper sheet, wherein the flap fastener is releasably affixed to the flap fastener cover.

* * * * *